United States Patent
Hua et al.

(10) Patent No.: US 11,697,805 B2
(45) Date of Patent: Jul. 11, 2023

(54) HIGH-FIDELITY POLYMERASE WITH PREFERENCE FOR GAPPED DNA AND USE THEREOF

(71) Applicant: Zhejiang University, Hangzhou (CN)

(72) Inventors: Yuejin Hua, Hangzhou (CN); Xingru Zhou, Hangzhou (CN); Liangyan Wang, Hangzhou (CN); Xuanyi Chen, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 78 days.

(21) Appl. No.: 17/229,653

(22) Filed: Apr. 13, 2021

(65) Prior Publication Data

US 2022/0017880 A1  Jan. 20, 2022

(30) Foreign Application Priority Data

Jul. 16, 2020  (CN) .......................... 202010687851.3

(51) Int. Cl.
*C12N 9/12* (2006.01)
*C07K 14/195* (2006.01)
*C12Q 1/6844* (2018.01)

(52) U.S. Cl.
CPC .......... *C12N 9/1252* (2013.01); *C07K 14/195* (2013.01); *C12Q 1/6844* (2013.01)

(58) Field of Classification Search
None
See application file for complete search history.

(56) References Cited

U.S. PATENT DOCUMENTS

| 9,428,737 B1* | 8/2016 | Gaucher | C12N 9/1252 |
| 2015/0184226 A1* | 7/2015 | Bauer | C12P 19/34 |
| | | | 435/6.12 |

OTHER PUBLICATIONS

Chica et al. CurrOpin Biotechnol. Aug. 2005;16(4):378-84. (Year: 2005).*
Singh et al. Curr Protein Pept Sci. 2017, 18, 1-11 (Year: 2017).*
Accession P52027. Oct. 1, 1996 (Year: 1996).*
Accession BDD80092. Oct. 6, 2016 (Year: 2018).*
Chinese First Office Action in corresponding Chinese Application No. 202010687851.3, dated Oct. 11, 2021.
Kathrin Heinz, et al. "Lesion Bypass Activity of DNA Polymerase A from the Extremely Radioresistant Organism Deinococcus radiodurans," The Journal of Biological Chemistry, Apr. 13, 2007, vol. 282, No. 15, pp. 10908-10914.
Dea Slade, et al., "Recombination and Relication in DNA Repair of Heavily Irradiated Deinococcus radiodurans," Cell 136, Mar. 20, 2009, pp. 1044-1055.
Gregory P. Mullen, et al., "Metal Binding to DNA Polymerase I, Its Large Fragment, and Two 3',5'-Exonuclease Mutants of the Large Fragment," The Journal of Biological Chemistry, Aug. 25, 1990, vol. 265, No. 24, pp. 14327-14334.

* cited by examiner

Primary Examiner — Christian L Fronda

(74) Attorney, Agent, or Firm — Leason Ellis LLP

(57) ABSTRACT

The disclosure provides a high-fidelity polymerase with preference for gapped DNA and use thereof. The Klenow fragment (KlenDr) derived from *Deinococcus radiodurans* DNA polymerase I, which has the high-fidelity polymerization characteristics, is independent of 3'-5' proofreading exonuclease activity, has the preference for binding gapped DNA, and is different from the existing commercial high-fidelity polymerase. Due to the specific affinity of KlenDr to gapped DNA substrate, the 3' end of the forward primer will not be cut off, and the downstream nucleotide chain is rarely replaced.

4 Claims, 4 Drawing Sheets

Specification includes a Sequence Listing.

FIG.3

HIGH-FIDELITY POLYMERASE WITH PREFERENCE FOR GAPPED DNA AND USE THEREOF

CROSS REFERENCE TO RELATED APPLICATION

This patent application claims the benefit and priority of Chinese Patent Application No. 202010687851.3 filed on Jul. 16, 2020, the disclosure of which is incorporated by reference herein in its entirety as part of the present application.

TECHNICAL FIELD

The disclosure belongs to the field of genetic engineering, and relates to a high-fidelity polymerase with preference for gapped DNA and use thereof.

BACKGROUND ART

DNA polymerase has an extensively using value in molecular cloning, DNA sequencing, library construction and other genetic engineering operations, and its ability for accurate DNA replication is important. At present, most of the commercially used high-fidelity DNA polymerases rely on the 3'-5' proofreading exonuclease activity. When the inserted nucleotides do not conform to the principle of Watson-Crick base complementary pairing, an inappropriate spatial conformation will force the newly inserted nucleotides to transfer from the polymerase active site to the 3'-5' exonuclease active site, thus cutting off the misincorporated nucleotides to ensure the accuracy of DNA replication. At present, the commercially used high-fidelity polymerase which does not depend on 3'-5' proofreading exonuclease activity is still unavailable.

DNA polymerase usually has the preference for DNA with primer-template structure. However, with the development of biotechnology, the diversity of researchers's demand for genetic modification is increasing. For example, the gap between linker and fragment needs to be filled in the construction of sequencing library based on T5 transposase, but there is no commercial polymerase with specific preference for binding gapped DNA. In addition, although most polymerases can fill the gap, they often have 3'-5' proofreading exonuclease activity, which will degrade the upstream nucleotide at 3' end. Although the polymerase with mutated proofreading exonuclease activity does not degrade the upstream nucleotide, its fidelity will be reduced, and the activity of strand displacement of nucleotide will be enhanced.

DNA polymerase I is the first DNA polymerase discovered by human beings, which has 5'-3' nuclease domain, 3'-5' exonuclease domain and DNA polymerase domain (as shown in FIG. 1). *E. coli* DNA polymerase I can be divided into 34 kDa small fragment and 74 kDa Klenow fragment after being treated with subtilisin (or trypsin). Klenow fragment contains 3'-5' exonuclease domain and DNA polymerase domain, which is a kind of DNA polymerase widely used in commerce. In 2007, Heinz et al. expressed and purified the protein homologous to KlenDr fragment of *E. coli* in *Deinococcus radiodurans* R1 in vitro, and reported its high-fidelity polymerization characteristics and weak ability of chain substitution synthesis, but there was no further study on substrate preference, so the polymerase shows limited application value up to now.

SUMMARY

In view of the diverse requirements for DNA polymerization applications in the current process of genetic engineering and sequencing library construction, the present disclosure deeply explores the polymerization characteristics of KlenDr, and provides a high-fidelity polymerase with preference for gapped DNA and use thereof.

A high-fidelity polymerase with preference for gapped DNA has high-fidelity polymerization characteristics independent of 3'-5' proofreading exonuclease activity, and preferentially binds gapped DNA. The DNA polymerase is derived from *Deinococcus radiodurans* R1, purchased from American Type Culture Collection, with a collection number of ATCC 13939, containing the amino acids 289-921 (protein sequence ID ANC71194.1) which is set forth in SEQ ID NO: 1.

In some embodiments, the high-fidelity polymerase with preference for gapped DNA may be used in nucleic acid amplification to fill the DNA gap.

In some embodiments, the reaction buffer of the nucleic acid amplification system contains 50-200 mM KCl, 20-30 mM Tris HCl with the pH of 7.5-8.0, 1-10 mM $MgCl_2$, 0.1-0.5 mM dNTPs, 0.1 mg/ml BSA and 1 mM DTT.

In some embodiments, the optimum reaction temperature of the nucleic acid amplification system is 25-37° C.

In some embodiments, the polymerase is suitable for genetic engineering operations where the DNA gaps need to be filled and sequencing library construction.

In some embodiments, the sequencing library construction includes library construction based on Tn5 transposon.

Compared with the prior art, the disclosure has the following beneficial effects:

(1) the KlenDr's high-fidelity polymerization is independent of 3'-5' proofreading exonuclease activity, which can avoid the degradation of forward primer chain and is suitable for nucleic acid amplification process without 3'-5' excision activity.

(2) KlenDr has the preference for binding gapped DNA, and has weak ability of strand replacement synthesis, so it is suitable for genetic engineering operations and sequencing library construction processes with the need to fill DNA gaps.

BRIEF DESCRIPTION OF THE DRAWINGS

Figure 3:
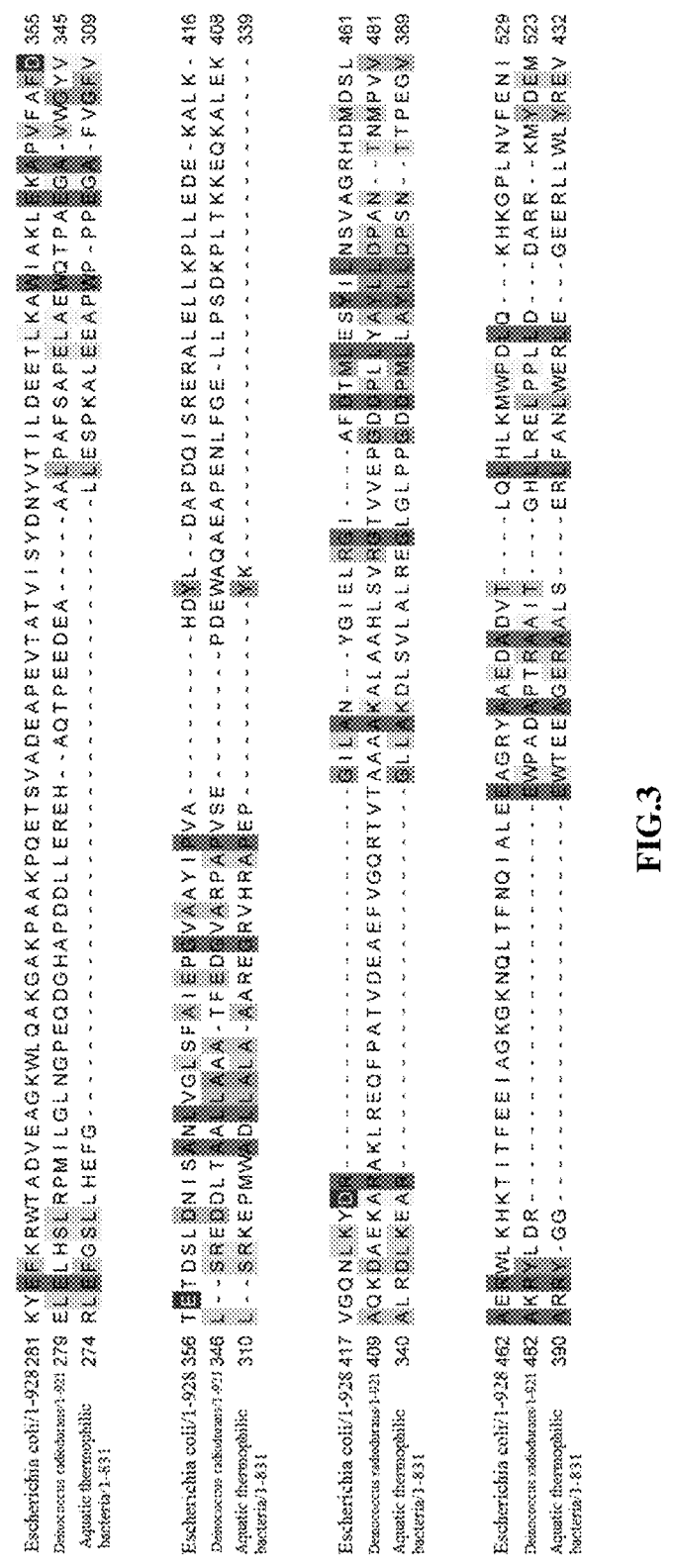

FIG. 3 shows a comparison of 3'-5' proofreading exonuclease activity between KlenDr and *E. coli* Klenow fragment.

DETAILED DESCRIPTION OF THE EMBODIMENTS

The present disclosure will be further explained with reference to the attached drawings and specific examples.

Example 1: Construction of KlenDr Protein Expression Strain of *Deinococcus radiodurans*

Figure 1:
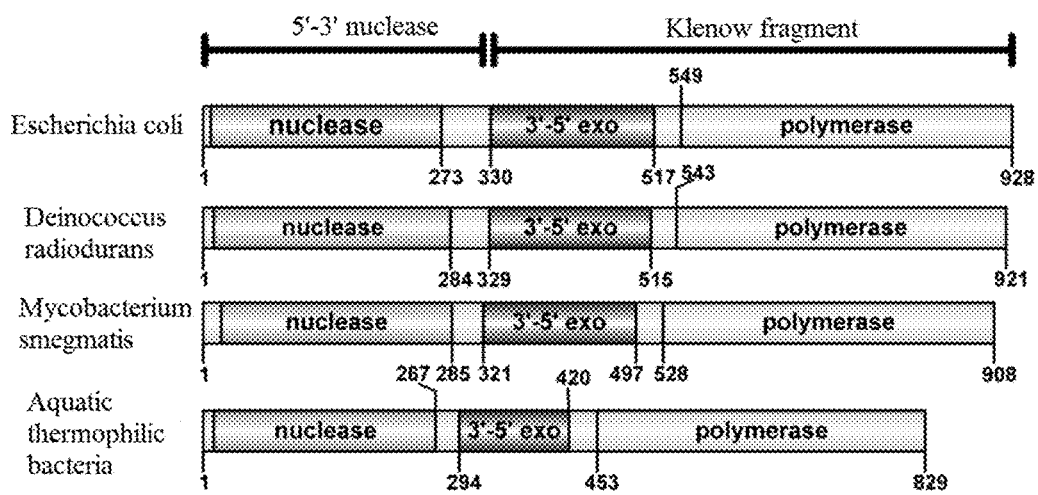
FIG. 1 is a schematic diagram shows domain of DNA polymerase I family.

According to the R1 genome (protein sequence ID: ASM163882v1) of *Deinococcus radiodurans* re-sequenced in 2016, DNA polymerase I (protein sequence ID: ANC71194.1) contains 921 amino acids, which is 35 amino acids less than the old version (protein sequence ID: ASM856v1). The KlenDr involved in the present disclosure is derived from the amino acids 289-921 of the new DNA polymerase I sequence. FIG. 1 is a schematic diagram of the domain of DNA polymerase I family, in which the domain of *Deinococcus radiodurans* is illustrated in the second bar of the figure.

(1) The genome of *Deinococcus radiodurans* R1 was extracted by using the bacterial genome DNA extraction kit (DP302-02, TIANGEN Biotech (Beijing)), and its concentration and purity were determined by NanoDrop 1000 (Thermo company);

(2) Based on the amino acids 289-921 of the new DNA polymerase I and pet28a plasmid, a pair of primers for homologous recombination was designed. The forward primer KlenDr-F (SEQ ID NO: 2) was: 5'-gtgccgcgcggcagc-catatgCTGGGGCTGAACGGGCCA-3', wherein the lower-case letter was the homologous fragment on pet28a vector, and the restriction site was NdeI; the reverse primer (SEQ ID NO: 3) was 5'-acggagctcgaattcggatccTCACTTCGTGT-CAAACCAGTTCG-3', wherein the lowercase letter was the homologous fragment on pet28a vector, and the restriction site was BamHI. With the genomic DNA of *Deinococcus radiodurans* R1 as the template, the target fragment (PCR product) was amplified by TransStart FastPfu DNA Polymerase (from TransGen Biotech), then the corresponding PCR product was purified and recovered by Wizard SV Gel and PCR Clean-Up kit;

(3) The KlenDr gene fragment was recombined into the pet28a vector linearized by NdeI/BamHI double enzyme digestion (N-terminal contains 6×His tag) by using Clon-Express II One Step Cloning recombinase system (from Vazyme Company) to obtain the recombinant product;

(4) The recombinant product was transformed into *E. coli* DH5a competent cells (from TransGen Biotech), and the cells were plated on a solid LB medium containing 40 µg/mL Kanamycin, and inverted cultured at 37° C. overnight;

(5) Several single colonies were selected and shaken cultured in 5 ml liquid LB medium containing 40 µg/mL Kanamycin at 37° C. for 10 h. Plasmids were extracted with Axygen plasmid extraction kit, and sequenced with T7/T7ter primer. After blasting the sequence for confirmation, the correct plasmids were then stored at −20° C.

Example 2: Induced Expression of KlenDr Protein of *Deinococcus radiodurans*

(1) Successfully constructed Pet28a-klenDr expression vector was transformed into *E. coli* BL21(DE3) expression strain (TransGen Biotech), and the successfully transformed clone strain was screened by solid LB medium containing 40 µg/mL Kanamycin and 34 µg/mL chloramphenicol antibiotics;

(2) The successfully transformed single colony was screened and cultured into 5 ml liquid culture medium, shaken cultured at 37° C. overnight, then the colony was transferred to 500 ml culture medium, and cultured until $OD_{600}$ was 0.6-0.8, placed on ice and cooled for 10 min, then 100 µl 1M IPTG was added, and the mixture was cultured at 30° C. for 5 h to induce the expression of target protein;

(3) After the induction, the bacteria were collected by centrifugation at 8000 rpm for 8 min, then washed with 1×PBS resuspension, finally centrifuged at 8000 rpm for 5 min, the supernatant was discarded, and the bacteria were stored at −80° C.

Example 3: Purification of KlenDr Protein of *Deinococcus radiodurans*

Figure 2:
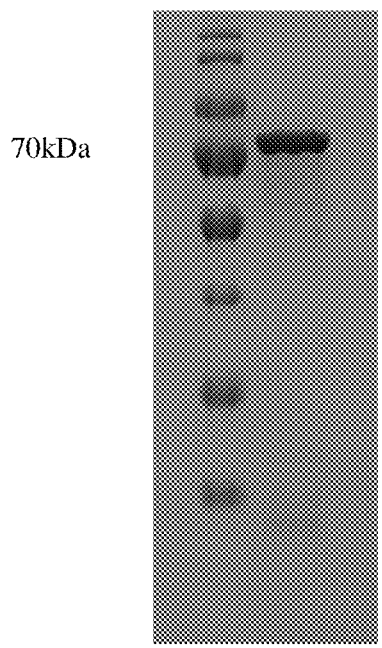
FIG. 2 is a SDS-PAGE gel electrophoresis diagram of purified KlenDr protein, which shows the purity of KlenDr protein is over 95%.

(1) Cell lysis: 15 mL lysis Buffer (300 mM NaCl, 20 mM Tris HCl pH 8.0, 5% Glycerol, 3 mM (3-Me, 10 mM imidazole) resuspend cells was added into 1 g bacteria (wet weight). The ultrasonic cell disruptor (JY92-IIN, Scientz, Ningbo) was used to disrupt cells in ice water bath until the suspension was transparent. The parameters were as follows: alternating rod φ6, power 60%, ultrasonic 2.5 s, clearance 9.9 s and period 60-90 min. The disrupted cell suspension was centrifuged at 15000 rpm for 35 min, the cell debris was removed, and the supernatant was retained and filtered with 0.22 µM or 0.45 µM filter membrane;

(2) Nickel column affinity purification: nickel column (HisTrap HP 1 ml) was purchased from GE HealthCare company. At first, the nickel column was balanced with Ni-bufferA (300 mM NaCl, 20 mM Tris HCl pH 8.0, 5% Glycerol, 3 mM (3-Me), and the cell lysate was fully combined with the nickel column at a flow rate of 1 ml/min. Then, gradient elution was carried out with 15%, 50% and 100% Ni-bufferB (300 mM NaCl, 20 mM Tris HCl pH 8.0, 5% Glycerol, 3 mM (3-Me, 300 mM Imidazole), respectively. The elute was detected by SDS-PAGE gel, and the target protein was eluted at 150 mM imidazole;

(3) Desalination: the HiTrap Desalting was purchased from GE HealthCare. The elute containing the target protein was collected and concentrated to less than 1 ml with GE ultrafiltration concentration tube (30 kDa), and loaded at 1 ml/min flow rate and eluted. The desalination buffer contained 20 mM Tris-HCl pH 8.0, 100 mM NaCl and 5% Glycerol;

(4) Heparin column purification: HiTrap Heparin HP column was purchased from GE HealthCare. Heprain-bufferA contains 20 mM Tris-HCl pH8.0, 100 mM NaCl and 5% Glycerol, and Heprain-bufferB contains 20 mM Tris-HCl pH8.0, 800 mM NaCl and 5% Glycerol. According to the linear gradient of 50 ml volume, the proportion of buffer B was increased to 100%, and the proteins appeared in peaks were collected. SDS-PAGE showed that the target protein was eluted at 35% buffer B;

(5) Molecular sieve purification: Superdex 200 Increase 10/300 GL was purchased from GE HealthCare company. The target protein was concentrated to a volume of about 500 µl by ultrafiltration tube (30 kDa). The molecular sieve buffer contained 20 mM Tris-HCl pH8.0, 100 mM KCl, 0.8 ml/min, and the target protein was loaded at 0.8 ml/min flow rate and eluted, the peak of the target protein appeared when the volume of the elution was 14.5 mL. SDS-PAGE electrophoresis showed that the molecular weight of the protein was about 70 kDa and the purity was over 95% (as shown in FIG. 2). After concentrating the target protein, the protein concentration was determined by NanoDrop instrument, and the protein was quickly frozen with liquid nitrogen and stored at −80° C.

Figure 4:
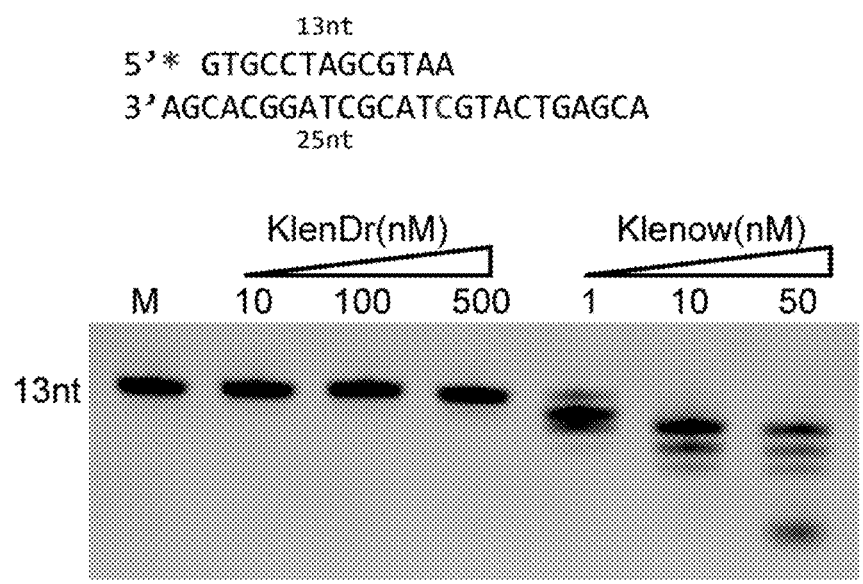
FIG. 4 is a multiple sequence comparison diagram of DNA polymerase I 3'-5' proofreading exonuclease domain in *Deinococcus radiodurans, E. coli* and *Thermus. aquaticus* bacteria; where the grey background represents conserved amino acids, and the arrows indicates conserved amino acids in the active site of Klenow fragment of *E. coli* (D355, E357, D424).

Example 4: KlenDr Protein of *Deinococcus radiodurans* does not have 3'-5' Proofreading Exonuclease Activity (1) Detection of KlenDr 3'-5' Proofreading Exonuclease Activity In Vitro:

A primer-template DNA sequence (SEQ ID NO: 4) with 3' end mismatch was synthesized by Shanghai Sangon Biotech. The primer sequence was 5'-CGTGCCTAGCGTA-3', wherein the 5' end was labeled with 6-FAM fluorescence, and the template sequence (SEQ ID NO: 5) was 5'-ACGAGTCATGCTACGCTAGGCACGA-3'. 100 μM of the primer sequence and 200 μM of the template sequence were added to 50 μl annealing system (20 mM Tris HCl pH8.0, 100 mM NaCl), respectively, and the primer-template structure with a final concentration of 2 μM was obtained;

In vitro enzymatic reaction system (10 μl) contained 100 mM NaCl, 20 mM Tris-HCl (pH 8.0), 0.1 mg/ml BSA, 1 mM DTT, 10-500 nM KlenDr, 5 mM MgCl$_2$ and 50 nM primer-template substrate with 3' end mismatch. After reacting at 37° C. for 10 mM, 5 μl quench buffer (90% formamide, 50 mM EDTA, 0.01% bromophenol blue) was added to stop the reaction, and the product was heated at 98° C. for 5 min to fully denature DNA, which was then immediately placed on ice for cooling. The product was separated with 15% TBE-urea-PAGE gel, the electrophoresis was conducted at 180V for 50 min, and gel was scanned and imaged with Typhoon 9500 instrument (GE Healthcare company). In this experiment, Klenow fragment (purchased from New England Biolabs) of *E. coli* was used as positive control for 3'-5' proofreading exonuclease activity;

Gel imaging results are shown in FIG. 3. Klenow fragment of *E. coli* shows obvious proofreading exonuclease activity at 10 nM, while KlenDr shows no exonuclease product at 500 nM, suggesting that KlenDr lacks 3'-5' proofreading exonuclease activity;

(2) Multi-sequence alignment of 3'-5' exonuclease domain in DNA polymerase I of *E. coli*, aquatic thermophilic bacteria and *Deinococcus radiodurans*:

In order to further confirm the 3'-5' proofreading exonuclease activity of KlenDr, we compared KlenDr with Klenow fragments of *E. coli* and *T. aquaticus* by multiple sequence alignment (FIG. 4). Important acidic amino acids, that can be combined with catalytic metal ions, in the 3'-5' exonuclease domain of *E. coli* Klenow include D355, E357 and D424 (indicated with arrows in FIG. 4). It is known that *T. aquaticus* lacks 3'-5' exonuclease due to the lacking of these amino acids, and KlenDr sequence also does not have these important amino acids in *E. coli* Klenow fragment, which further confirms KlenDr's lack of proofreading exonuclease activity.

Example 5: KlenDr Protein of *Deinococcus radiodurans* Prefers to Bind Gapped DNA The template sequence (SEQ ID NO: 6) was 5'-GATGT-CAAGCAGTCCTAACTTTTTTTGAGGCAGAGTCC-3', the forward primer sequence (SEQ ID NO: 7) was 5'-FAM-GGACTCTGCCTCAA-3', the reverse primer sequence was 5'-AGTTAGGACTGCTTGACATC-3', and the 5' end of the forward primer sequence was marked with 6-FAM label. 200 μM Template, 100 μM forward and 200 μM reverse primer sequences were added to 50 μl annealing system (20 mM Tris HCl pH8.0, 100 mM NaCl) respectively, and the gapped DNA structure with a final concentration of 2 μM was obtained. The template sequence (SEQ ID NO: 8) of primer-template structure was 5'-ACGAGTCATGT-TACGCTAGGCACGA-3', and the annealing procedure was the same as Example 1.

The binding reaction system (10 μl) of KlenDr protein of *Deinococcus radiodurans*, double-stranded gapped DNA and primer template DNA included: 50 nM FAM labeled substrate, 50-5000 nM KlenDr or Klenow, 100 mM NaCl, 20 mM Tris-HCl (pH 8.0), 0.1 mg/ml BSA, 1 mM DTT, 5 mM EDTA. The reaction system was incubated at 37° C. for 30 min, added with 5 μl native loading buffer (20 mM tris-HCl pH 8.0, 100 mM NaCl, 20% glycerol), separated by 10% Native-PAGE electrophoresis, and scanned and imaged with Typhoon 9500 instrument (GE Healthcare company).

Figure 5:
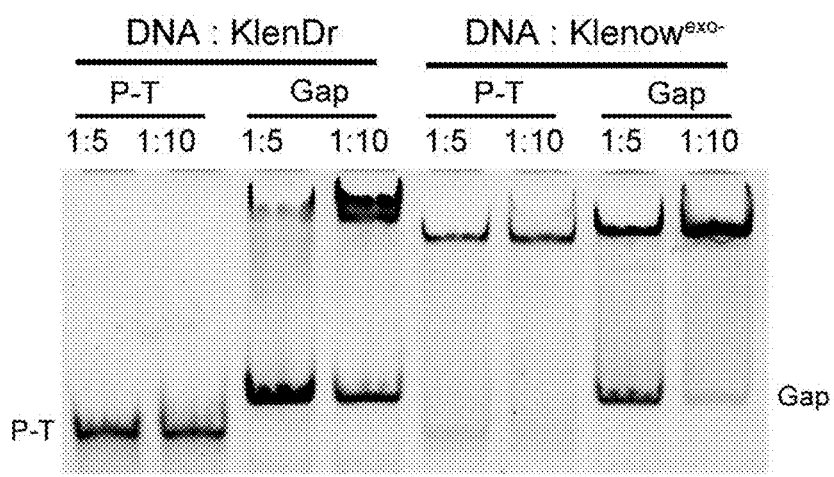
FIG. 5 shows a comparison of the binding affinity of KlenDr and *E. coli* Klenow fragment to primer-template structure and gapped DNA structure respectively.

As shown in FIG. 5, KlenDr has the preference for binding double-stranded gapped DNA substrate instead of primer-template structure, which is contrary to the substrate preference of *E. coli* Klenow fragment for binding primer-template structure.

Example 6: Use of KlenDr Protein of *Deinococcus radiodurans* in Filling Double-Stranded Gap As Klenow fragment of *E. coli* can cut off the 3' end of the forward primer, Klenow$^{xo-}$ with mutated proofreading exonuclease activity was used as the control (purchased from New England Biolabs).

The reaction system (10 μl) for filling the DNA gap with KlenDr protein of *Deinococcus radiodurans* included 100 nM FAM labeled substrate, 100 nM KlenDr or Klenow$^{exo-}$, 100 mM NaCl, 20 mM Tris-HCl (pH 8.0), 0.1 mg/ml BSA, 1 mM DTT, 5 mM MgCl$_2$, 1-50 μM dNTPs. The sequence and way for formation of double-stranded gapped DNA structure were the same as that in Example 2. The reaction system was incubated at 37° C. for 20 min, then 5 μl quench buffer was added to stop the reaction, and the product was heated at 98° C. for 5 min to fully denature the DNA, which was then immediately cooled on ice. The product was separated with 15% TBE-urea-PAGE gel, the electrophoresis was conducted at 180V for 50 min, and the gel was scanned and imaged with Typhoon 9500 (GE Healthcare company).

Figure 6:
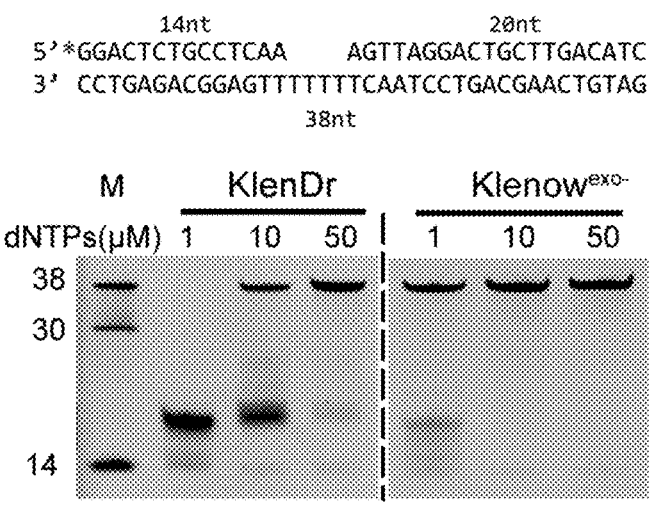
FIG. 6 shows a comparison of the gap-filling activity between KlenDr and *E. coli* Klenow fragment.

As shown in FIG. 6, KlenDr has an obvious pause after filling the gap, while Klenow of the control group has stronger ability of strand substitution synthesis, so KlenDr is more suitable for filling the gap in nucleic acid amplification and polymerization scenarios.

Figure 7:
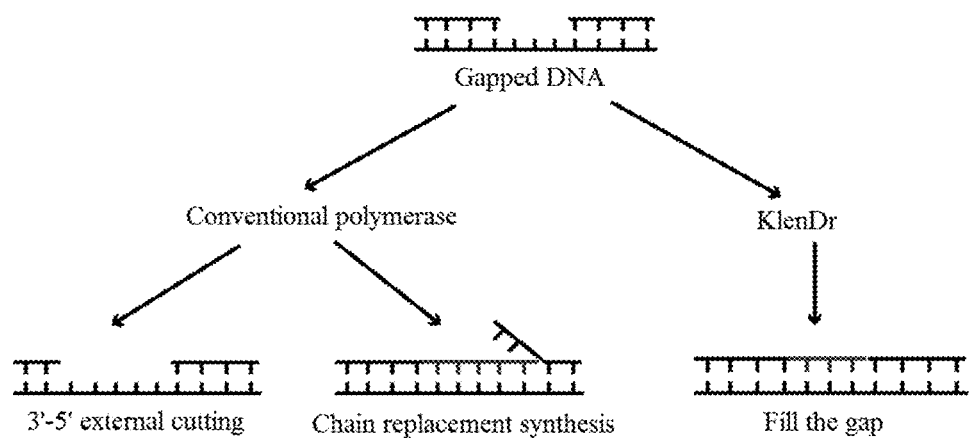
FIG. 7 is a schematic diagram of DNA gap treated by conventional polymerase and KlenDr.

Example 7: Use of KlenDr in the Method for Library Construction Based on Tn5 Transposon The method for library construction based on Tn5 transposon is widely used in the second generation sequencing, especially in the chromatin open sequencing technology (ATAC-Seq). Its principle for library construction is as follows: firstly, Tn5 transposase is used to insert linker sequence into DNA double strand, and two Tn5 insertions can form a complete library. Then, DNA polymerase is used to make up the gap caused by T5 transposition, and ligase is used for ligation. Finally, the library can be amplified by PCR amplification. As shown in FIG. 7, KlenDr in the present disclosure is very suitable for gap filling process, which not only has specific binding preference for gapped DNA, but also ensures the accuracy of inserting nucleotides without degrading forward nucleotides, and rarely replaces and synthesizes downstream nucleotide chains, which will effectively improve the efficiency of the whole library construction process.

The above is only the preferred embodiment of the present disclosure, but the present disclosure is not limited to the above detailed methods. According to the teaching and enlightenment of the present disclosure, anyone who is familiar with this technical scheme, using the polymerase characteristics of KlenDr disclosed in the present disclosure to perform nucleic acid amplification, etc., is within the scope of protection of the present disclosure.

---

What is claimed is:

1. A method for amplifying a nucleic acid with a DNA gap, comprising filling the DNA gap with a *Deinococcus radiodurans* polymerase with preference for gapped DNA, wherein the *Deinococcus radiodurans* polymerase comprises the amino acid sequence of SEQ ID NO: 1.

2. The method according to claim 1, wherein a reaction buffer for amplification contains 50-200 mM KCl, 20-30 mM Tris HCl with the pH of 7.5-8.0, 1-10 mM $MgCl_2$, 0.1-0.5 mM dNTPs, 0.1 mg/ml BSA and 1 mM DTT.

3. The method according to claim 1, wherein an optimum reaction temperature for amplification is in a range of 25-37° C.

4. The method according to claim 3, wherein a reaction buffer for amplification contains 50-200 mM KCl, 20-30 mM Tris HCl with the pH of 7.5-8.0, 1-10 mM $MgCl_2$, 0.1-0.5 mM dNTPs, 0.1 mg/ml BSA and 1 mM DTT.

* * * * *

SEQUENCE LISTING

```
<160> NUMBER OF SEQ ID NOS: 8

<210> SEQ ID NO 1
<211> LENGTH: 632
<212> TYPE: PRT
<213> ORGANISM: Artificial sequence
<220> FEATURE:
<223> OTHER INFORMATION: Deinococcus radiodurans R1

<400> SEQUENCE: 1

Leu Gly Leu Asn Gly Pro Glu Gln Asp Gly His Ala Pro Asp Asp Leu
1               5                   10                  15

Leu Glu Arg Glu His Ala Gln Thr Pro Glu Glu Asp Glu Ala Ala Ala
            20                  25                  30

Leu Pro Ala Phe Ser Ala Pro Glu Leu Ala Glu Trp Gln Thr Pro Ala
        35                  40                  45

Glu Gly Ala Val Trp Gly Tyr Val Leu Ser Arg Glu Asp Asp Leu Thr
    50                  55                  60

Ala Ala Leu Leu Ala Ala Ala Thr Phe Glu Asp Gly Val Ala Arg Pro
65                  70                  75                  80

Ala Pro Val Ser Glu Pro Asp Glu Trp Ala Gln Ala Glu Ala Pro Glu
                85                  90                  95

Asn Leu Phe Gly Glu Leu Leu Pro Ser Asp Lys Pro Leu Thr Lys Lys
            100                 105                 110

Glu Gln Lys Ala Leu Glu Lys Ala Gln Lys Asp Ala Glu Lys Ala Arg
        115                 120                 125

Ala Lys Leu Arg Glu Gln Phe Pro Ala Thr Val Asp Glu Ala Glu Phe
    130                 135                 140

Val Gly Gln Arg Thr Val Thr Ala Ala Ala Lys Ala Leu Ala Ala
145                 150                 155                 160

His Leu Ser Val Arg Gly Thr Val Val Glu Pro Gly Asp Asp Pro Leu
                165                 170                 175

Leu Tyr Ala Tyr Leu Leu Asp Pro Ala Asn Thr Asn Met Pro Val Val
            180                 185                 190

Ala Lys Arg Tyr Leu Asp Arg Glu Trp Pro Ala Asp Ala Pro Thr Arg
        195                 200                 205

Ala Ala Ile Thr Gly His Leu Leu Arg Glu Leu Pro Pro Leu Leu Asp
    210                 215                 220

Asp Ala Arg Arg Lys Met Tyr Asp Glu Met Glu Lys Pro Leu Ser Gly
225                 230                 235                 240

Val Leu Gly Arg Met Glu Val Arg Gly Val Gln Val Asp Ser Asp Phe
                245                 250                 255

Leu Gln Thr Leu Ser Ile Gln Ala Gly Val Arg Leu Ala Asp Leu Glu
            260                 265                 270

Ser Gln Ile His Glu Tyr Ala Gly Glu Glu Phe His Ile Arg Ser Pro
        275                 280                 285

Lys Gln Leu Glu Thr Val Leu Tyr Asp Lys Leu Glu Leu Ala Ser Ser
    290                 295                 300

Lys Lys Thr Lys Leu Thr Gly Gln Arg Ser Thr Ala Val Ser Ala Leu
```

```
                305                 310                 315                 320
        Glu Pro Leu Arg Asp Ala His Pro Ile Ile Pro Leu Val Leu Glu Phe
                        325                 330                 335

Arg Glu Leu Asp Lys Leu Arg Gly Thr Tyr Leu Asp Pro Ile Pro Asn
                        340                 345                 350

Leu Val Asn Pro His Thr Gly Arg Leu His Thr Thr Phe Ala Gln Thr
                        355                 360                 365

Ala Val Ala Thr Gly Arg Leu Ser Ser Leu Asn Pro Asn Leu Gln Asn
                        370                 375                 380

Ile Pro Ile Arg Ser Glu Leu Gly Arg Glu Ile Arg Lys Gly Phe Ile
        385                 390                 395                 400

Ala Glu Asp Gly Phe Thr Leu Ile Ala Ala Asp Tyr Ser Gln Ile Glu
                        405                 410                 415

Leu Arg Leu Leu Ala His Ile Ala Asp Asp Pro Leu Met Gln Gln Ala
                        420                 425                 430

Phe Val Glu Gly Ala Asp Ile His Arg Arg Thr Ala Ala Gln Val Leu
                        435                 440                 445

Gly Leu Asp Glu Ala Thr Val Asp Ala Asn Gln Arg Arg Ala Ala Lys
                        450                 455                 460

Thr Val Asn Phe Gly Val Leu Tyr Gly Met Ser Ala His Arg Leu Ser
        465                 470                 475                 480

Asn Asp Leu Gly Ile Pro Tyr Ala Glu Ala Thr Phe Ile Glu Ile
                        485                 490                 495

Tyr Phe Ala Thr Tyr Pro Gly Ile Arg Arg Tyr Ile Asn His Thr Leu
                        500                 505                 510

Asp Phe Gly Arg Thr His Gly Tyr Val Glu Thr Leu Tyr Gly Arg Arg
                        515                 520                 525

Arg Tyr Val Pro Gly Leu Ser Ser Arg Asn Arg Val Gln Arg Glu Ala
                        530                 535                 540

Glu Glu Arg Leu Ala Tyr Asn Met Pro Ile Gln Gly Thr Ala Ala Asp
        545                 550                 555                 560

Ile Met Lys Leu Ala Met Val Gln Leu Asp Pro Gln Leu Asp Ala Ile
                        565                 570                 575

Gly Ala Arg Met Leu Leu Gln Val His Asp Glu Leu Leu Ile Glu Ala
                        580                 585                 590

Pro Leu Asp Lys Ala Glu Gln Val Ala Ala Leu Thr Lys Lys Val Met
                        595                 600                 605

Glu Asn Val Val Gln Leu Lys Val Pro Leu Ala Val Glu Val Gly Thr
                        610                 615                 620

Gly Pro Asn Trp Phe Asp Thr Lys
        625                 630

<210> SEQ ID NO 2
<211> LENGTH: 39
<212> TYPE: DNA
<213> ORGANISM: Artificial sequence
<220> FEATURE:
<223> OTHER INFORMATION: forward primer KlenDr-F

<400> SEQUENCE: 2
gtgccgcgcg gcagccatat gctggggctg aacgggcca                              39

<210> SEQ ID NO 3
<211> LENGTH: 44
<212> TYPE: DNA
<213> ORGANISM: Artificial sequence
```

```
<220> FEATURE:
<223> OTHER INFORMATION: reverse primer KlenDr-F

<400> SEQUENCE: 3
acggagctcg aattcggatc ctcacttcgt gtcaaaccag ttcg         44

<210> SEQ ID NO 4
<211> LENGTH: 13
<212> TYPE: DNA
<213> ORGANISM: Artificial sequence
<220> FEATURE:
<223> OTHER INFORMATION: primer-template DNA sequence with 3' end
      mismatch

<400> SEQUENCE: 4
cgtgcctagc gta                                            13

<210> SEQ ID NO 5
<211> LENGTH: 25
<212> TYPE: DNA
<213> ORGANISM: Artificial sequence
<220> FEATURE:
<223> OTHER INFORMATION: primer-template DNA sequence with 5' end
      labeled with 6-FAM fluorescence

<400> SEQUENCE: 5
acgagtcatg ctacgctagg cacga                               25

<210> SEQ ID NO 6
<211> LENGTH: 38
<212> TYPE: DNA
<213> ORGANISM: Artificial sequence
<220> FEATURE:
<223> OTHER INFORMATION: template sequence

<400> SEQUENCE: 6
gatgtcaagc agtcctaact tttttgagg cagagtcc                  38

<210> SEQ ID NO 7
<211> LENGTH: 14
<212> TYPE: DNA
<213> ORGANISM: Artificial sequence
<220> FEATURE:
<223> OTHER INFORMATION: forward primer sequence

<400> SEQUENCE: 7
ggactctgcc tcaa                                           14

<210> SEQ ID NO 8
<211> LENGTH: 25
<212> TYPE: DNA
<213> ORGANISM: Artificial sequence
<220> FEATURE:
<223> OTHER INFORMATION: template sequence of primer-template structur

<400> SEQUENCE: 8
acgagtcatg ttacgctagg cacga                               25
```